United States Patent [19]
Francese

[11] Patent Number: 5,394,885
[45] Date of Patent: Mar. 7, 1995

[54] ENDOSCOPIC BIOPSY FORCEPS JAWS AND INSTRUMENT INCORPORATING SAME

[75] Inventor: Jose L. Francese, Miami Springs, Fla.

[73] Assignee: Symbiosis Corporation, Miami, Fla.

[21] Appl. No.: 177,536

[22] Filed: Jan. 5, 1994

[51] Int. Cl.⁶ .............................................. A61B 10/00
[52] U.S. Cl. ...................................... 128/751; 606/207
[58] Field of Search .................... 606/51, 52, 205–211, 606/173; 128/750–755; 294/99.1; 81/419, 424.5

[56] References Cited

U.S. PATENT DOCUMENTS

| | | | |
|---|---|---|---|
| 3,515,139 | 6/1970 | Mallina | 606/207 |
| 3,608,554 | 9/1971 | McGuinness et al. | 606/207 |
| 5,059,214 | 10/1991 | Akopov et al. | 606/207 |
| 5,228,451 | 7/1993 | Bales et al. | 128/751 |
| 5,263,967 | 11/1993 | Lyons, III et al. | 606/208 |

*Primary Examiner*—Stephen C. Pellegrino
*Assistant Examiner*—William W. Lewis
*Attorney, Agent, or Firm*—David P. Gordon

[57] ABSTRACT

Biopsy forceps jaws have a cup portion defined by a cup wall having an outer portion with a cup wall edge, and an inner portion having teeth. The teeth include peaks and valleys with the peaks rising above the outer portion cup wall edge, and the valleys remaining below the outer portion cup wall edge. The teeth are preferably arranged radially around at least a portion of the periphery of the cup and are offset by one half pitch so that two opposed identical jaws will mate. The radially outer surface of the peaks and the radially inner surface of the valleys are preferably radially chamfered. When two opposed jaws close, the peaks of the teeth on one jaw enter the valleys of the teeth on the other jaw and the edges of the cup walls of the two jaws touch such that the teeth of the two jaws are fully enclosed by the outer portions of the cup walls and the outer surface of the closed jaws is completely smooth. Also, during closure, as the radially chamfered peaks of the teeth of one jaw enter the radially chamfered valleys of the teeth of the other jaw, moving points of contact between the outer edges of the peaks and the cup wall edge above the valleys cause a scissoring action. A biopsy forceps instrument incorporating the jaws is also disclosed.

27 Claims, 2 Drawing Sheets

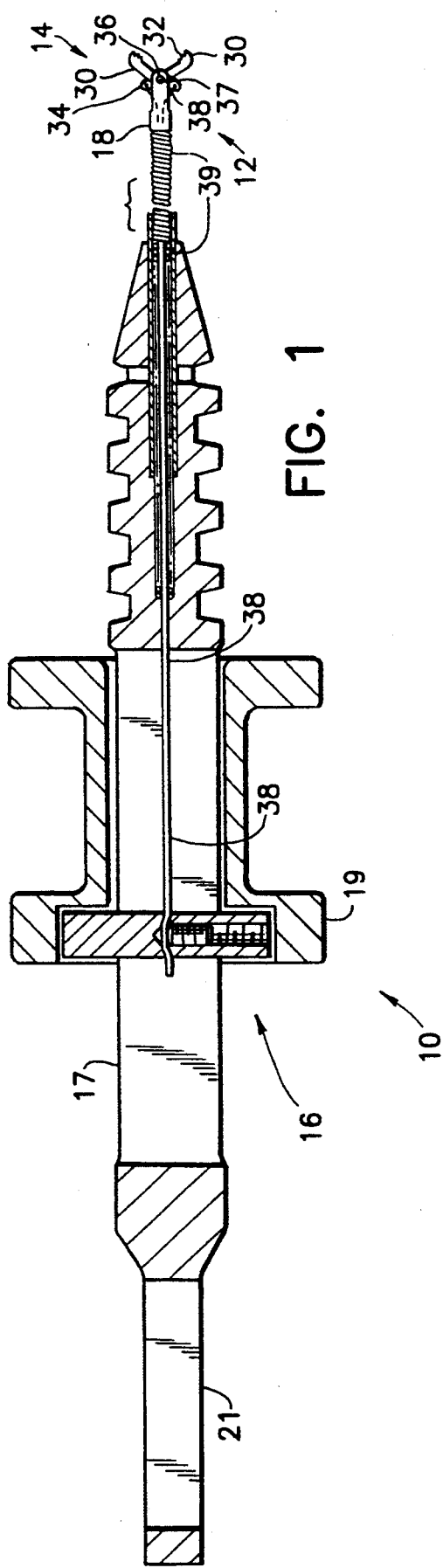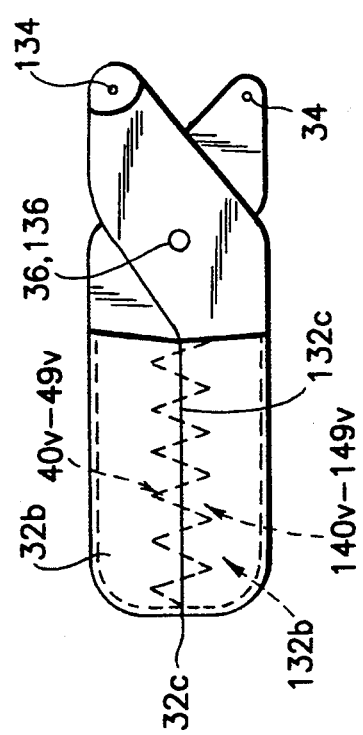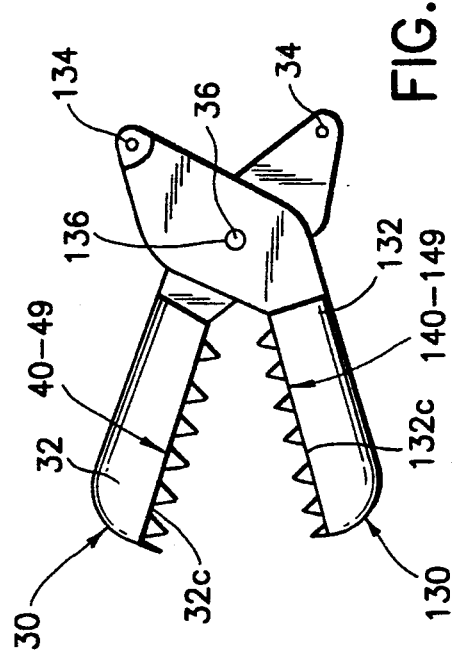

ENDOSCOPIC BIOPSY FORCEPS JAWS AND INSTRUMENT INCORPORATING SAME

BACKGROUND OF THE INVENTION

1. Field of the Invention

The present invention relates to endoscopic biopsy forceps devices. In particular, the invention relates to biopsy forceps jaws having a shielding structure which enshrouds the sharp edges of the teeth of the jaws when the teeth of the jaws are in a closed position.

2. State of the Art

Endoscopic biopsy forceps are used for taking tissue samples from the human body for analysis. These forceps typically have a pair of cupped jaws attached to the distal end of a long flexible coil, the proximal end of which is attached to actuating means which opens and closes the jaws when the actuating means is manipulated by the practitioner. The endoscopic biopsy procedure is accomplished through an endoscope which is inserted into a body and guided by manipulation to the biopsy site. The endoscope typically includes a long narrow flexible tube carrying distal optical means and having a narrow lumen for receiving the biopsy forceps. The practitioner guides the endoscope to the biopsy site using the optical means and inserts the forceps, with jaws closed, through the lumen of the endoscope to the biopsy site. While viewing the biopsy site through the optical means of the endoscope, the practitioner opens the forceps jaws and carefully guides the jaws around a tissue to be sampled. When the jaws are in the correct position, the practitioner manipulates the actuating means and closes the jaws on the tissue to be sampled. The cupped jaws grip the tissue and enclose a sample of the tissue in the space between the cupped jaws. The forceps are then withdrawn from the lumen of the endoscope while the jaws are kept shut, with the sample captured in the space between the cupped jaws typically torn away from the tissue at the biopsy site.

The endoscopic biopsy procedure poses several challenges to the design and manufacture of biopsy forceps and particularly biopsy forceps jaws. The jaws must be small enough to fit through the narrow lumen of the endoscope, yet strong enough and sharp enough to cut and/or tear tissue. An early example of an endoscopic biopsy forceps is shown in U.S. Pat. No. 3,895,636 to Schmidt. The forceps in Schmidt include a pair of cupped toothless jaws with sharpened opposed edges intended to cut through tissue being sampled. Due to the miniature size of the jaws, however, it is difficult to sharpen the edges to a very high degree. Consequently, it is necessary to apply great force to the jaws in order to sever the tissue being sampled. In practice, sufficient force to sever the tissue is rarely achieved. Thus, either the jaws effect a clamping action which permits the tissue to be torn away from the biopsy site, or the jaws simply slip off the tissue without cutting or tearing it.

U.S. Pat. No. 4,880,015 to Neirman shows endoscopic biopsy forceps having opposed rectangularly cupped jaws with teeth on their parallel edges. When the jaws close, opposed teeth interleave providing a slightly better gripping ability than the jaws disclosed by Schmidt. However, the rectangular configuration of the jaws and the absence of teeth at the distal end of the jaws limits their functionality. Additionally, with these jaws and other toothed jaws, the teeth often do not align properly and prevent the jaws from closing completely which adds to the inefficiency of cutting and/or tearing. Similarly, the misalignment of the opposed teeth sometimes causes the jaws to lock in the closed position.

Co-owned U.S. Pat. No. 5,228,451 to Bales et al., the complete disclosure of which is hereby incorporated by reference herein, discloses endoscopic biopsy forceps having a pair of opposed jaws with teeth which extend along the entire opposed edge of each jaw. The teeth are offset by one-half pitch so that the upper jaw and lower jaw can be made from the same mold and still allow the teeth to align (interleave) when the jaws are closed. This arrangement of jaw teeth greatly improves the cutting and/or gripping (tearing) action of the forceps. It is a perceived problem, however, that this arrangement of teeth may expose a rough outer surface even when the jaws are closed during their entry into and exit from the lumen of the endoscope. It is believed that the perceived rough outer surface of the closed jaws might cause damage or undue wear to the lumen of the endoscope.

SUMMARY OF THE INVENTION

It is therefore an object of this invention to provide toothed endoscopic biopsy forceps jaws which have a smooth outer surface when closed.

It is also an object of this invention to provide toothed endoscopic biopsy forceps jaws having superior cutting and/or tearing ability.

It is another object of this invention to provide biopsy forceps jaws having teeth which align to allow the jaws to close completely without locking.

It is a further object of this invention to provide biopsy forceps jaws which enhance cutting ability by using a scissoring action.

It is also an object of this invention to provide a biopsy forceps incorporating toothed jaws which are self-aligning, have a smooth outer surface when closed, and which also provide enhanced cutting and/or tearing ability.

In accord with these objects which will be discussed in detail below, the biopsy forceps jaws according to the invention each have a cup with an appropriate tang extending from a proximal end of the cup for mounting the jaw in a conventional manner. The cup of the jaw has a relatively thick wall with an outer side portion having a cup edge and an inner side portion in which teeth are formed. The teeth are defined by peaks and valleys formed in the inner side portion of the wall of the cup such that the peaks of the teeth rise above the edge and the valleys remain below the edge of the outer side portion of the cup wall. In order to form the teeth in the inner side portion of the wall, the radial thickness of the teeth is less than the radial thickness of the cup wall, thereby causing the radially outer surface of the teeth to be spaced radially inward from the outer surface of the cup wall. With the cups of the jaws so arranged, when the two opposed jaws close, the peaks of the teeth on one jaw enter the valleys of the teeth on the other jaw and the edges of the cup walls of the two jaws touch. In the closed position, the teeth of the two jaws are enclosed by the cup walls and the outer surface of the closed jaws is smooth.

In accord with a preferred aspect of the invention, the cups of the jaws are provided with the general shape of an oblate hemisphere or a portion of an oblate hemisphere, and the teeth are radially arranged around at least a portion of the periphery of the cup and are offset by one half pitch so that two opposed identical jaws will mate as described in co-owned U.S. Pat. No. 5,228,451 to Bales et al. In addition, the radially outer surface of the peaks and the radially inner surface of the valleys are radially chamfered. Thus, as the radially chamfered peaks of the teeth of one jaw enter the radially chamfered valleys of the teeth of the other jaw, moving points of contact between the outer edges of the peaks and the cup wall edge above the valleys cause a scissoring action when the jaws are near fully closed.

According to another aspect of the invention, the jaws of the invention are mounted in a conventional manner on a clevis at the distal end of a biopsy forceps coil and are coupled by their tangs to a pair of pull wires within the coil. The proximal end of the coil is provided with a manual actuating means which moves the pull wires within the coil to open and close the jaws in a conventional manner.

Additional objects and advantages of the invention will become apparent to those skilled in the art upon reference to the detailed description taken in conjunction with the provided figures.

BRIEF DESCRIPTION OF THE DRAWINGS

FIG. 1 is a longitudinal cross sectional view of an endoscopic biopsy forceps instrument incorporating the biopsy forceps jaws of the invention.

FIG. 3 is an enlarged side elevation view of a pair of biopsy forceps jaws according to the invention in an open position; and FIG. 4 is a side elevation view of the jaws of FIG. 3 in a closed position.

DETAILED DESCRIPTION OF THE PREFERRED EMBODIMENT

Figure 2:
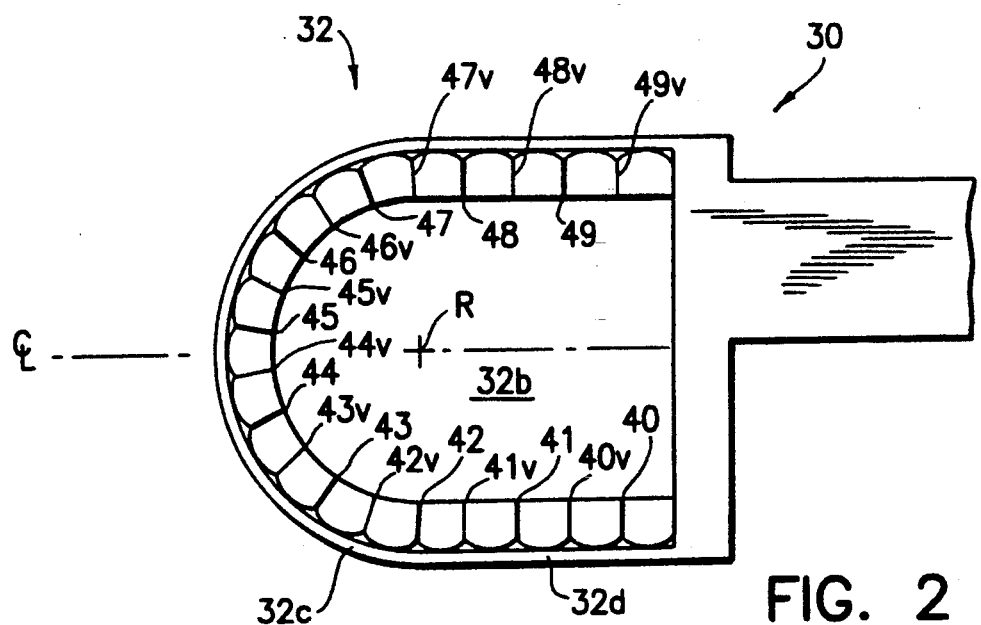
FIG. 2 is an enlarged top plan view of a biopsy forceps jaw according to the invention.

Referring now to FIG. 1, an endoscopic biopsy forceps instrument 10 is shown with a distal end 12 having a biopsy jaw assembly 14, and a proximal end 16 having a handle 17, a spool 19 and a thumb ring 21. The biopsy jaw assembly 14 generally includes a clevis 18 and a pair of identical jaws 30. Each identical jaw 30 has a distal toothed cup 32, a proximal tang 34, and a transverse mounting bore 36. The jaws 30 are mounted on the clevis 18 by a pin 37 which passes through their mounting bores 36. The proximal tang 34 of each jaw is coupled to the distal end of a pull wire 38 which extends through a hollow member or coil 39. The proximal end of each pull wire 38 is coupled to the spool 19 which is slidably attached to the handle 17. The jaws are opened and closed by movement of the spool 19 relative to the handle 17 as described more fully in co-owned U.S. Pat. No. 5,228,451 to Bales et al.

Figure 2A:
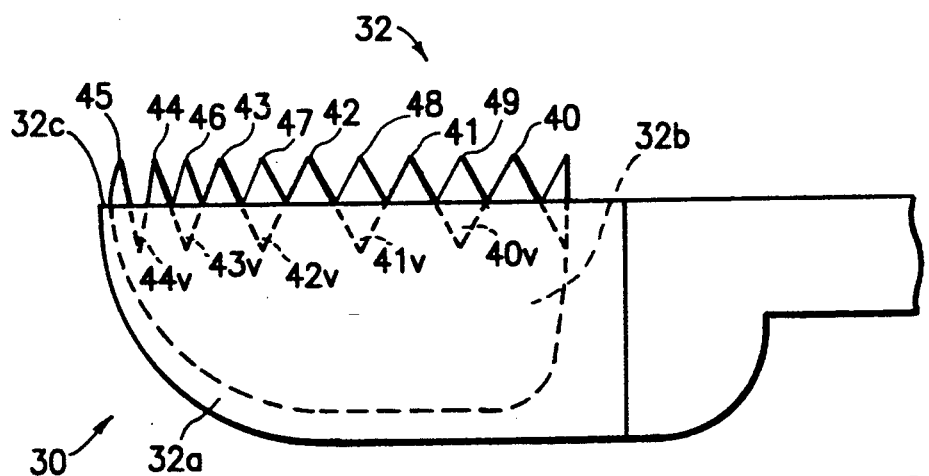
FIG. 2a is a side elevation view of the jaw of FIG. 2.
Figure 2B:
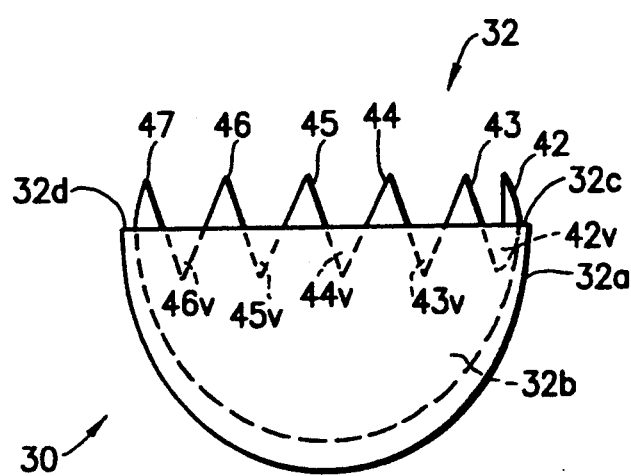
FIG. 2b is a distal end view of the jaw of FIG. 2.

As seen in FIGS. 2, 2a, and 2b, the distal toothed cup 32 of each jaw 30 is formed by a cup wall 32a which defines a container-like recess 32b. The upper edge 32c of the cup wall 32a is provided with an array of substantially triangular sharp tooth peaks (teeth) 40–49, each of which is separated by a substantially triangular tooth valley (recess) 40v–49v. As seen best in FIG. 2, the distal end of the toothed cup 32 is provided with tooth peaks 43–47 and tooth valleys 42v–46v which are radially directed about a point "R" as described more fully in co-owned U.S. Pat. No. 5,228,451 to Bales et al. Additionally, tooth peaks 48, 49 and tooth valleys 47v–49v on one side of the longitudinal centerline of the cup 32 are displaced by one half pitch from tooth peaks 40–42 and tooth valleys 40v, 41v on the other side of the centerline of the cup 32. This radial arrangement and half pitch displacement provides for self-alignment and the ability to use a single cast to make a pair of identical mating jaws as described in U.S. Pat. No. 5,228,451 to Bales et al As shown in FIG. 2, the radial thickness of the tooth peaks and tooth valleys is less than the radial thickness of the cup wall 32a, so that the upper edge 32c of the cup wall 32a has an outer lip 32d.

As seen best in FIGS. 2a and 2b, according to the present invention, the tooth peaks 40–49 rise above the upper edge 32c of the cup wall 32a and the tooth valleys 40v–49v extend below the upper edge 32c of the cup wall 32a. This arrangement provides for the shielding of the teeth when the jaws are closed as shown in FIG. 4. Those skilled in the art will appreciate that when the jaws are closed, the teeth from one jaw enter the valleys or recesses of the opposed jaw. As shown in FIGS. 2a and 2b, it will also be appreciated that both the peaks and the valleys are radially chamfered as best seen with reference to tooth 45 in FIG. 2a, teeth 42 and 47 in FIG. 2b, and valley 42v in FIG. 2b. The radius of the chamfer preferably either corresponds to, or is smaller than the radius of the curved cup wall 32a. The radial chamfering aids in preventing the tooth peaks of one jaw from becoming locked in the tooth valleys of an opposed jaw when the jaws are closed. The outer lip 32d of the upper edge 32c of the cup wall 32a may be sharpened, particularly in the portions which pass over the valleys 40v–49v. By varying the radius of the chamfer of the tooth peaks and tooth valleys so that at least a lower portion of the tooth peaks frictionally engage an upper portion of the tooth valleys, a scissor-like action can be provided at the sharpened upper edge 32c of the cup wall 32a as tooth peaks enter tooth valleys from a near closed to a fully closed position. In other words, by forming the portion of the tooth closest to the cup edge with a first radius which corresponds to the radius of the curved cup wall 32a, and the portion of the tooth which is most distant from the cup edge with a smaller radius, cutting will occur at the cup edge while at the same time there will be sufficient clearance over the remainder of the surfaces to prevent locking. Those skilled in the art will appreciated, however, that there is always a trade-off between the amount of scissor-like action provided at the cup edge and the possibility of the jaws locking due to frictional forces.

Referring now to FIGS. 3 and 4, a pair of identical jaws 30, 130 are mounted by their mounting holes 36, 136 for relative rotation from an open position as seen in FIG. 3 to a closed position as seen in FIG. 4. Opening and closing of the jaws is effected as described above through the movement of pull wires coupled to the tangs 34, 134 of the jaws. When in the open position, each jaw 30, 130 exposes its tooth peaks 40–49, 140–149 so that a tissue (not shown) may be grasped between the opposed jaws. As the jaws are moved from the open position toward the closed position, the tooth peaks engage a portion of the tissue between the jaws and bite into it. When the jaws are fully closed as shown in FIG. 4, a portion of the tissue is trapped in the container-like recesses 32b, 132b of the jaws, with the tooth peaks 40–49 of the jaw 30 residing in the tooth valleys 140v–149v of the jaw 130, and the tooth peaks 140–149 of the jaw 130 residing in the tooth valleys 40v–49v of the jaw 30. Upon completely closing, the upper edges 32c, 132c touch and, if sharpened, cut the trapped portion of the tissue away from the remaining portion of the tissue grasped. In addition, if the radius of the chamfer of the teeth corresponds to the cup walls (at any point), as the jaws are moved from a near closed position to a fully closed position, a scissor-like action between the teeth of one jaw and the sharpened upper edge of an opposed jaw will sever the trapped portion of the tissue along the sharpened upper edge. Regardless of whether or not cutting action is obtained, when the jaws are closed, the jaws present a substantially smooth outer surface.

The biopsy forceps jaws of the present invention provide improved cutting and tearing action while also presenting a smooth outer surface when the jaws are closed. The smooth outer surface of the closed jaws eliminates or minimizes the possibility of endoscope damage or undue wear as the closed jaws are moved through the lumen of the endoscope. In addition, the radial arrangement and half pitch offset of the tooth peaks and valleys allows a self-aligning mating pair of biopsy forceps jaws to be cast from a single mold.

There have been described and illustrated herein an endoscopic biopsy forceps jaw having tooth peaks and tooth valleys arranged relative to the upper edge of the jaw cup wall such that when two jaws are closed together, the tooth peaks of one jaw are shielded within the cup wall of the other jaw. While particular embodiments of the invention have been described, it is not intended that the invention be limited thereto, as it is intended that the invention be as broad in scope as the art will allow and that the specifications be read likewise. Thus, while certain features the invention provide for a pair of identical jaws, the jaws need not be identical to achieve the shielding feature of the invention. Also, while the jaws have been shown in connection with a particular biopsy forceps instrument, it will be understood that the jaws could be used in conjunction with other types of medical instruments. In addition, while the jaws have been shown in a double acting embodiment, i.e., where both jaws rotate relative to each other, it will be understood that the jaws could also be used in a single acting embodiment where one jaw remains stationary and only the other jaw is rotated. Also, while the jaws have been shown as having substantially oblate hemispherical cups with radially chamfered tooth peaks and tooth valleys, it will be appreciated that the shape of the jaw cups and the type of chamfering or lack of chamfering may be varied without departing from the spirit of the invention as claimed. Moreover, while the jaws have been shown as having substantially triangular tooth peaks and substantially triangular tooth valleys, it will be understood that other shapes could be used and that the the shape of the valleys need not be the same shape as the peaks so long as the peaks fit into the valleys. In this regard, it will also be understood that a first jaw could be provided with only tooth valleys (i.e., the peaks are at or below the cup edge), while a second jaw is provided with only tooth peaks (i.e., the valleys are at or above the cup edge) so that the peaks on the second jaw enter the valleys of the first jaw when the jaws are closed.

It should also be appreciated by those skilled in the art that while the jaws of the invention were described as being formed via casting, other forming techniques known in the art such as MIM can be utilized. Also, while the teeth, valleys, and edges of the jaws of the invention were described directionally (i.e., extending above, below, etc.), it will be appreciated that the directional description is for purposes of clarity and is relative to the orientation of the jaws. It will therefore be appreciated by those skilled in the art that yet other modifications could be made to the provided invention without deviating from its spirit and scope as so claimed.

I claim:

1. A biopsy forceps jaw assembly, comprising:
   a pair of jaws, at least one of which is rotatable relative to the other from an open position to a closed position, each of said jaws having a substantially hollow distal cup defined by a cup wall having an exterior portion with an upper edge and an interior portion, a first one of said jaws having at least one cutting tooth extending upward from said interior portion of said cup wall past said upper edge of said exterior portion of said cup wall, and a second one of said jaws having at least one recess in said interior portion of said cup wall, said recess extending downward from said upper edge of said exterior portion of said cup wall, wherein said cutting tooth on said interior portion of said cup wall of said first one of said jaws enters said recess on said interior portion of said cup wall of said second one of said jaws when said jaws are in the closed position so that said cutting tooth is at least partially covered by said cup wall of said second one of said jaws.

2. A biopsy forceps jaw assembly according to claim 1, wherein:
   said interior portion of said cup wall of said jaw having said recess is curved, and
   said tooth is radially chamfered.

3. A biopsy forceps jaw assembly according to claim 2, wherein:
   said interior portion of said cup wall of said jaw having said tooth is curved, and
   said recess is radially chamfered.

4. A biopsy forceps jaw assembly according to claim 1, wherein:
   said edge of said exterior portion of said cup wall of at least one of said jaws is sharpened.

5. A biopsy forceps jaw assembly according to claim 1, wherein:
   said first one of said jaws has a plurality of teeth extending from said interior portion of said cup wall upward past said edge of said exterior portion of said cup wall,
   said second one of said jaws has a plurality of recesses in said interior portion of said cup wall, said recesses extending downward past said edge of said exterior portion of said cup wall, and
   each of said teeth on said first one of said jaws enters a respective one of said recesses on said second one of said jaws when said jaws are in the closed position so that said teeth are at least partially covered by said cup wall of said second one of said jaws.

6. A biopsy forceps jaw assembly according to claim 5, wherein:
   each of said jaws has a curved distal end, and
   at least some of said teeth and said recesses are radially arranged around said curved distal end.

7. A biopsy forceps jaw assembly according to claim 5, wherein:
   said first one of said jaws also has a plurality of recesses in said interior portion of said cup wall, said recesses extending downward past said edge of said exterior portion of said cup wall, and said second one of said jaws also has a plurality of teeth extending upward from said interior portion of said cup wall past said edge of said exterior portion of cup wall, and each of said teeth on said second one of said jaws enters a respective one of said recesses on said first one of said jaws when said jaws are in the closed position so that said teeth are at least partially covered by said cup wall of said first one of said jaws.

8. A biopsy forceps jaw assembly according to claim 7, wherein:

said teeth and recesses on said first one of said jaws alternate in position around said interior portion of said cup wall so that each tooth is separated from an adjacent tooth by a recess.

9. A biopsy forceps jaw assembly according to claim 8, wherein:

said first one of said jaws has a longitudinal centerline, said teeth on a first side of said longitudinal centerline being displaced by one half pitch from corresponding teeth on a second side of said longitudinal centerline.

10. A biopsy forceps jaw assembly according to claim 9, wherein:

said first one of said jaws and said second one of said jaws are substantially identical.

11. A biopsy forceps jaw assembly according to claim 1, wherein:

said exterior portion of said cup wall of each jaw is arranged such that when said pair of jaws are in a closed position relative to each other, the exterior portions of the cup walls of the jaws present a substantially smooth outer surface.

12. A biopsy forceps jaw assembly according to claim 5, wherein:

said exterior portion of said cup wall of each jaw is arranged such that when said pair of jaws are in a closed position relative to each other, the exterior portions of the cup walls of the jaws present a substantially smooth outer surface, and said plurality of teeth are enclosed by said said exterior portions of the cup walls.

13. A biopsy forceps apparatus, comprising:

a) a hollow member having distal and proximal ends;
b) opposed first and second jaws, said first jaw being rotatably disposed on said distal end of said hollow member; and
c) actuation means having a distal end coupled to said first jaw, said actuation means for effecting articulation of said first jaw from an open to a closed position relative to said second jaw, wherein each of said opposed first and second jaws has a substantially hollow distal cup defined by a cup wall having an exterior portion with an upper edge and an interior portion, a first one of said jaws having at least one tooth extending upward from said interior portion of said cup wall past said upper edge of said exterior portion of said cup wall, and a second one of said jaws having at least one recess in said interior portion of said cup wall, said recess extending downward from said upper edge of said exterior portion of said cup wall, wherein said tooth on said interior portion of said cup wall of said first one of said jaws enters said recess on said interior portion of said cup wall of said second one of said jaws when said jaws are in the closed position so that said cutting tooth is at least partially covered by said cup wall of said second one of said jaws.

14. A biopsy forceps apparatus according to claim 13, further comprising:

d) clevis means coupled to said hollow member and to said first and second jaws, said clevis means for rotatingly disposing said first jaw relative to said distal end of said hollow member.

15. A biopsy forceps apparatus according to claim 14, wherein:

said second jaw is rotatingly disposed relative to said distal end of said hollow member.

16. A biopsy forceps apparatus according to claim 13, wherein:

said interior portion of said cup wall of said jaw having said recess is curved, and
said tooth is radially chamfered.

17. A biopsy forceps apparatus according to claim 16, wherein:

said interior portion of said cup wall of said jaw having said tooth is curved, and
said recess is radially chamfered.

18. A biopsy forceps apparatus according to claim 13, wherein:

said edge of said exterior portion of said cup wall of at least one of said jaws is sharpened.

19. A biopsy forceps apparatus according to claim 13, wherein:

said first one of said jaws has a plurality of teeth extending from said interior portion of said cup wall upward past said edge of said exterior portion of said cup wall, said second one of said jaws has a plurality of recesses in said interior portion of said cup wall, said recesses extending downward past said edge of said exterior portion of said cup wall, and each of said teeth on said first one of said jaws enters a respective one of said recesses on said second one of said jaws when said jaws are in the closed position so that said teeth are at least partially covered by said cup wall of said second one of said jaws.

20. A biopsy forceps apparatus according to claim 19, wherein:

each of said jaws has a curved distal end; and
at least some of said teeth and said recesses are radially arranged around said curved distal end.

21. A biopsy forceps apparatus according to claim 19, wherein:

said first one of said jaws also has a plurality of recesses in said interior portion of said cup wall, said recesses extending downward past said edge of said exterior portion of said cup wall, and said second one of said jaws also has a plurality of teeth extending upward from said interior portion of said cup wall past said edge of said exterior portion of said cup wall, and each of said teeth on said second one of said jaws enters a respective one of said recesses on said first one of said jaws when said jaws are in the closed position so that said teeth are at least partially covered by said cup wall of said first one of said jaws.

22. A biopsy forceps apparatus according to claim 21, wherein:

said teeth and recesses on said first one of said jaws alternate in position around said interior portion of said cup wall so that each tooth is separated from an adjacent tooth by a recess.

23. A biopsy forceps apparatus according to claim 22, wherein:

said first one of said jaws has a longitudinal centerline, said teeth on a first side of said longitudinal centerline being displaced by one half pitch from corresponding teeth on a second side of said longitudinal centerline.

24. A biopsy forceps apparatus according to claim 23, wherein:
said first one of said jaws and said second one of said jaws are substantially identical.

25. A biopsy forceps apparatus according to claim 13, wherein:
said exterior portion of said cup wall of each jaw is arranged such that when said pair of jaws are in a closed position relative to each other, the exterior portions of the cup walls of the jaws present a substantially smooth outer surface.

26. A biopsy forceps apparatus according to claim 19, wherein:
said exterior portion of said cup wall of each jaw is arranged such that when said pair of jaws are in a closed position relative to each other, the exterior portions of the cup walls of the jaws present a substantially smooth outer surface, and said plurality of teeth are enclosed by said said exterior portions of the cup walls.

27. A biopsy forceps apparatus according to claim 13, wherein:
said hollow member is a coil.

* * * * *